(12) United States Patent
Lor et al.

(10) Patent No.: US 11,045,117 B2
(45) Date of Patent: Jun. 29, 2021

(54) SYSTEMS AND METHODS FOR DETERMINING AXIAL ORIENTATION AND LOCATION OF A USER'S WRIST

(71) Applicant: Apple Inc., Cupertino, CA (US)

(72) Inventors: Jason Lor, San Francisco, CA (US); Siddharth Nangia, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 275 days.

(21) Appl. No.: 16/124,055

(22) Filed: Sep. 6, 2018

(65) Prior Publication Data

US 2019/0000354 A1 Jan. 3, 2019

Related U.S. Application Data

(62) Division of application No. 15/705,644, filed on Sep. 15, 2017, now Pat. No. 10,478,099.

(Continued)

(51) Int. Cl.
*A61B 5/11* (2006.01)
*A63B 24/00* (2006.01)
(Continued)

(52) U.S. Cl.
CPC .......... *A61B 5/1122* (2013.01); *A61B 5/681* (2013.01); *A63B 24/0006* (2013.01);
(Continued)

(58) Field of Classification Search
USPC ..................................................... 73/379.01
See application file for complete search history.

(56) References Cited

U.S. PATENT DOCUMENTS

| 5,483,261 | A | 1/1996 | Yasutake |
|---|---|---|---|
| 5,488,204 | A | 1/1996 | Mead et al. |

(Continued)

FOREIGN PATENT DOCUMENTS

| EP | 2 290 583 A1 | 3/2011 |
|---|---|---|
| EP | 2 698 686 A2 | 2/2014 |

(Continued)

OTHER PUBLICATIONS

Eisenstein, J. S. et al. (May 2, 2001). "Analysis of Clustering Techniques to Detect Hand Signs," *Intelligent Multimedia, Video and Speech Processing, of 2001 International Symposium*, Piscataway, NJ, USA, IEEE, pp: 259-262.

(Continued)

*Primary Examiner* — Octavia Hollington
(74) *Attorney, Agent, or Firm* — Brownstein Hyatt Farber Schreck, LLP

(57) ABSTRACT

The provided disclosure relates to systems and methods for determining the axial orientation and location of a user's wrist using one or more sensors located on the strap, the device underbody, or both. For example, the strap can include a plurality of elastic sections and a plurality of rigid sections. Each elastic section can include one or more flex sensors. In some examples, one or more electromyography (EMG) sensors can be included to measure the user's electrical signals, and the user's muscle activity can be determined. In some examples, a plurality of strain gauges can be included to generate one or more signals indicative of any changes in shape, size, and/or physical properties of the user's wrist. In some examples, the device can include a plurality of capacitance sensors for increased granularity and/or sensitivity in measuring the amount of tension exerted by the user's wrist.

20 Claims, 8 Drawing Sheets

Related U.S. Application Data

(60) Provisional application No. 62/398,338, filed on Sep. 22, 2016.

(51) Int. Cl.

| | | |
|---|---|---|
| *G01L 1/14* | (2006.01) | |
| *G01L 1/16* | (2006.01) | |
| *A61B 5/00* | (2006.01) | |
| *G06F 3/01* | (2006.01) | |
| *A61B 5/024* | (2006.01) | |
| *A63B 71/06* | (2006.01) | |
| *A61B 5/06* | (2006.01) | |
| *G01P 13/00* | (2006.01) | |
| *A61B 5/22* | (2006.01) | |
| *A61B 5/296* | (2021.01) | |

(52) U.S. Cl.
CPC .......... *A63B 24/0062* (2013.01); *G01L 1/146* (2013.01); *G01L 1/16* (2013.01); *G06F 3/011* (2013.01); *A61B 5/02416* (2013.01); *A61B 5/067* (2013.01); *A61B 5/1112* (2013.01); *A61B 5/1118* (2013.01); *A61B 5/224* (2013.01); *A61B 5/296* (2021.01); *A61B 5/486* (2013.01); *A61B 5/6886* (2013.01); *A61B 2562/0214* (2013.01); *A63B 71/0619* (2013.01); *A63B 2024/0012* (2013.01); *A63B 2071/0663* (2013.01); *A63B 2220/40* (2013.01); *A63B 2220/50* (2013.01); *A63B 2220/803* (2013.01); *A63B 2220/836* (2013.01); *A63B 2230/08* (2013.01); *A63B 2230/60* (2013.01); *G01P 13/00* (2013.01); *G06F 3/017* (2013.01)

(56) References Cited

U.S. PATENT DOCUMENTS

| | | | |
|---|---|---|---|
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,244,873 B1 | 6/2001 | Hill et al. | |
| 6,265,978 B1 * | 7/2001 | Atlas | G08B 21/06 340/573.1 |
| 6,310,610 B1 | 10/2001 | Beaton et al. | |
| 6,323,846 B1 | 11/2001 | Westerman et al. | |
| 6,547,728 B1 * | 4/2003 | Cornuejols | G04B 25/04 600/300 |
| 6,570,557 B1 | 5/2003 | Westerman et al. | |
| 6,677,932 B1 | 1/2004 | Westerman | |
| 6,690,387 B2 | 2/2004 | Zimmerman et al. | |
| 6,888,536 B2 | 5/2005 | Westerman et al. | |
| 7,015,894 B2 | 3/2006 | Morohoshi | |
| 7,156,819 B2 * | 1/2007 | Sieller | A61F 5/013 602/21 |
| 7,184,064 B2 | 2/2007 | Zimmerman et al. | |
| 7,218,226 B2 | 5/2007 | Wehrenberg | |
| 7,547,282 B2 | 6/2009 | Lo et al. | |
| 7,570,295 B2 | 8/2009 | Funato | |
| 7,614,008 B2 | 11/2009 | Ording | |
| 7,616,110 B2 | 11/2009 | Crump et al. | |
| 7,633,076 B2 | 12/2009 | Huppi et al. | |
| 7,653,883 B2 | 1/2010 | Hotelling et al. | |
| 7,657,849 B2 | 2/2010 | Imran et al. | |
| 7,663,607 B2 | 2/2010 | Hotelling et al. | |
| 7,688,306 B2 | 3/2010 | Wehrenberg et al. | |
| 7,844,914 B2 | 11/2010 | Andre et al. | |
| 7,957,762 B2 | 6/2011 | Herz et al. | |
| 8,006,002 B2 | 8/2011 | Kalayjian et al. | |
| 8,170,656 B2 | 5/2012 | Tan et al. | |
| 8,239,784 B2 | 8/2012 | Hotelling et al. | |
| 8,279,180 B2 | 10/2012 | Hotelling et al. | |
| 8,378,811 B2 | 2/2013 | Crump et al. | |
| 8,381,135 B2 | 2/2013 | Hotelling et al. | |
| 8,436,810 B2 | 5/2013 | Langereis et al. | |
| 8,447,704 B2 | 5/2013 | Tan et al. | |
| 8,479,122 B2 | 7/2013 | Hotelling et al. | |
| 8,618,930 B2 | 12/2013 | Papadopoulos et al. | |
| 8,634,808 B1 | 1/2014 | Zhong et al. | |
| 8,684,924 B2 * | 4/2014 | Ouwerkerk | A61M 21/00 600/301 |
| 8,963,806 B1 | 2/2015 | Starner et al. | |
| 9,044,149 B2 | 6/2015 | Richards et al. | |
| 9,081,542 B2 | 7/2015 | Dickinson et al. | |
| 9,265,449 B2 | 2/2016 | Donaldson | |
| 9,348,458 B2 | 5/2016 | Hotelling et al. | |
| 9,389,694 B2 | 7/2016 | Ataee et al. | |
| 9,592,007 B2 | 3/2017 | Nuovoo et al. | |
| 9,668,676 B2 | 6/2017 | Culbert | |
| 9,770,185 B2 | 9/2017 | Wheeler et al. | |
| 9,811,648 B2 | 11/2017 | Choi et al. | |
| 9,848,825 B2 | 12/2017 | Morris et al. | |
| 9,880,632 B2 | 1/2018 | Ataee et al. | |
| 9,933,937 B2 | 4/2018 | Lemay et al. | |
| 9,939,899 B2 | 4/2018 | Allec et al. | |
| 9,946,395 B2 | 4/2018 | Zhang et al. | |
| 10,042,422 B2 | 8/2018 | Morun et al. | |
| 10,088,924 B1 | 10/2018 | Ivanchenko | |
| 10,152,082 B2 | 12/2018 | Bailey | |
| 2002/0024500 A1 | 2/2002 | Howard | |
| 2005/0234351 A1 | 10/2005 | Nishii et al. | |
| 2006/0033724 A1 | 2/2006 | Chaudhri et al. | |
| 2006/0197753 A1 | 9/2006 | Hotelling | |
| 2008/0300055 A1 | 12/2008 | Lutnick et al. | |
| 2009/0174578 A1 | 7/2009 | Taki | |
| 2009/0306487 A1 | 12/2009 | Crowe et al. | |
| 2010/0182126 A1 | 7/2010 | Martis et al. | |
| 2010/0289772 A1 | 11/2010 | Miller | |
| 2011/0054360 A1 | 3/2011 | Son et al. | |
| 2011/0148568 A1 | 6/2011 | Lim et al. | |
| 2011/0173204 A1 | 7/2011 | Murillo et al. | |
| 2011/0235926 A1 | 9/2011 | Yokono | |
| 2012/0059298 A1 * | 3/2012 | Hoffman | A61N 1/36003 602/21 |
| 2012/0127070 A1 | 5/2012 | Ryoo et al. | |
| 2012/0188158 A1 | 7/2012 | Tan et al. | |
| 2013/0331234 A1 * | 12/2013 | Niederman | A63B 21/0005 482/46 |
| 2014/0028546 A1 | 1/2014 | Jeon et al. | |
| 2014/0031698 A1 | 1/2014 | Moon et al. | |
| 2014/0094675 A1 | 4/2014 | Luna | |
| 2014/0155705 A1 | 6/2014 | Papadopoulos et al. | |
| 2014/0240103 A1 | 8/2014 | Lake et al. | |
| 2014/0282270 A1 | 9/2014 | Slonneger | |
| 2015/0019135 A1 | 1/2015 | Kacyvenski et al. | |
| 2015/0084860 A1 | 3/2015 | Aleem et al. | |
| 2015/0193102 A1 | 7/2015 | Lanier et al. | |
| 2015/0366504 A1 | 12/2015 | Connor | |
| 2015/0370333 A1 | 12/2015 | Ataee et al. | |
| 2016/0085296 A1 * | 3/2016 | Mo | G06F 1/163 345/156 |
| 2016/0091980 A1 | 3/2016 | Baranski | |
| 2017/0031453 A1 | 2/2017 | Presura | |
| 2018/0078183 A1 | 3/2018 | Lor et al. | |
| 2018/0196514 A1 | 7/2018 | Allec et al. | |
| 2018/0307314 A1 | 10/2018 | Connor | |
| 2019/0220099 A1 | 7/2019 | Baranski et al. | |

FOREIGN PATENT DOCUMENTS

| | | |
|---|---|---|
| JP | 2000-163031 A | 6/2000 |
| JP | 2002-342033 A | 11/2002 |
| KR | 2012-0054809 A | 5/2012 |
| WO | WO-2012/138663 A2 | 10/2012 |
| WO | WO-2014/117125 A1 | 7/2014 |
| WO | WO-2015/060856 A1 | 4/2015 |
| WO | WO-2015/119637 A1 | 8/2015 |
| WO | WO-2015/121100 A1 | 8/2015 |

(56) References Cited

FOREIGN PATENT DOCUMENTS

WO    WO-2016/053459 A1    4/2016
WO    WO-2017/052957 A1    3/2017

OTHER PUBLICATIONS

Final Office Action dated Mar. 10, 2017, for U.S. Appl. No. 14/616,573, filed Feb. 6, 2015, five pages.
Final Office Action dated Aug. 31, 2018, for U.S. Appl. No. 14/616,573, filed Feb. 6, 2015, 20 pages.
International Search Report dated Mar. 21, 2016, for PCT Application No. PCT/US2015/042978, filed Jul. 30, 2015, six pages.
International Search Report dated Nov. 7, 2016, for PCT Application No. PCT/US2016/048582, filed Aug. 25, 2016, five pages.
Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.
Morganti, E. et al. (2012). "A smart watch with embedded sensors to recognize objects, grasps and forearm gestures," SciVerse ScienceDirect, Engineering Procedia, available online at www.sciencedirect.com, pp. 1169-1175.
Non-Final Office Action dated Jun. 16, 2016, for U.S. Appl. No. 14/616,573, filed Feb. 6, 2015, eleven pages.
Non-Final Office Action dated Dec. 21, 2016, for U.S. Appl. No. 15/038,419, filed May 20, 2016, twelve pages.
Non-Final Office Action dated Apr. 20, 2017, for U.S. Appl. No. 14/973,573, filed Dec. 17, 2015, 33 pages.
Non-Final Office Action dated Jun. 14, 2017, for U.S. Appl. No. 14/616,573, filed Feb. 6, 2015, 12 pages.
Non-Final Office Action dated Jun. 14, 2017, for U.S. Appl. No. 14/616,573, filed Feb. 6, 2015, twelve pages.
Non-Final Office Action dated Dec. 18, 2017, for U.S. Appl. No. 14/616,573, filed Feb. 6, 2015, 19 pages.
Notice of Allowance dated Apr. 3, 2017, for U.S. Appl. No. 15/038,419, filed May 20, 2016, ten pages.
Notice of Allowance dated Nov. 30, 2017, for U.S. Appl. No. 14/973,573, filed Dec. 17, 2015, 8 pages.
Reuss, J.L., et al. (Oct. 23-26, 2002). "Period Domain Analysis in Fetal Pulse Oximetry," Proceedings of the Second Joint EMBS/BMES Conference, Houston, TX, two pages.
Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.
Rubine, D.H. (May 1992). "Combining Gestures and Direct Manipulation," CHI '92, pp. 659-660.
U.S. Appl. No. 14/616,573, filed Feb. 6, 2015, entitled, "Motion and Gesture Input From a Wearable Device."
Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.
Zhao, S. et al. (Nov. 5, 2014). "Wireless Photoplethysmograph Knuckle Sensor System for Measuring Finger Motions," *2014 International Symposium on Optomechatronic Technologies, IEEE*, pp. 205-209, XP032783703.
Zheng, N. et al. (Oct. 17, 2011) "An Efficient User Verification System via Mouse Movements," Computer and Communications Security, ACM, 2 Penn Plaza, New York, NY, USA, pp. 139-150, XP058006047, DOI: 10.1145/2046707.2046725 ISBN: 978-1-4503-0948-6.
Non-Final Office Action dated Mar. 19, 2019, for U.S. Appl. No. 15/705,644, filed Sep. 15, 2017, 18 pages.
Notice of Allowance dated Jan. 9, 2019, for U.S. Appl. No. 14/616,573, filed Feb. 6, 2015, 9 pages.
Non-Final Office Action dated Sep. 11, 2018, for U.S. Appl. No. 15/705,644, filed Sep. 15, 2017, 19 pages.
Non-Final Office Action dated Mar. 29, 2019, for U.S. Appl. No. 15/914,838, filed Mar. 7, 2018, 19 pages.

\* cited by examiner

SYSTEMS AND METHODS FOR DETERMINING AXIAL ORIENTATION AND LOCATION OF A USER'S WRIST

CROSS REFERENCE TO RELATED APPLICATIONS

This application is a divisional of U.S. patent application Ser. No. 15/705,644, filed Sep. 15, 2017, and published on Mar. 22, 2018 as U.S. Patent Publication No. 2018-0078183 which claims the benefit under 35 USC 119(e) of U.S. Patent Application No. 62/398,338, filed Sep. 22, 2016, the contents of which are incorporated herein by reference in their entirety for all purposes.

FIELD OF THE DISCLOSURE

This relates to systems and method for determining axial orientation and location of a user's wrist.

BACKGROUND OF THE DISCLOSURE

Mobile electronic devices, such as mobile phones, smart phones, table computers, media players, and the like, have become quite popular. Many users carry a device almost everywhere they go and use their devices for a variety of purposes, including making and receiving phone calls, sending and receiving text messages and emails, navigation (e.g., using maps and/or a GPS receiver), purchasing items in a store (e.g., using contactless payment systems), and/or accessing the Internet (e.g., to look up information).

A user's mobile device may not always be readily accessible. For instance, when a mobile device receives a phone call, the device may be in a user's bag or pocket, and the user may be walking, driving, carrying something, or involved in other activity that can make it inconvenient or impossible for the user to reach into the bag or pocket to find the device.

A wearable device can assist with accessibility of information from the mobile device. In some examples, the user's movements can lead to frequent changes in the configuration and/or orientation of the wearable device relative to the user's wrist. In some instances, measurements regarding the user's mobility and functions can be skewed.

SUMMARY OF THE DISCLOSURE

This relates to systems and methods for determining the axial orientation and location of the user's wrist. The axial orientation and location can be determined using one or more sensors located on the strap, the device underbody, or both. For example, the strap (attached to the device underbody) can include a plurality of elastic sections and a plurality of rigid sections. Each elastic section can include one or more flex sensors. The flex sensors can be sensors configured to generate one or more signals indicative of the expansion or contractions of the user's wrist due to extension or tension, for example. In some examples, on or more electromyography (EMG) sensors can be included to measure the user's electrical signals, and the user's muscle activity can be determined. Measurements from the EMG sensors can be used in conjunction with one or more other sensor measurements, such as PPG sensor measurements, to determine one or more user characteristics. In some examples, a plurality of strain gauges (e.g., piezoelectric sensors) can be included to generate one or more signals indicative of any changes in shape, size, and/or physical properties of the user's wrist. In some examples, the device can include a plurality of capacitance sensors for increased granularity and/or sensitivity in measuring the amount of tension exerted by the user's wrist. The systems and methods disclosed can include analysis and feedback to a user regarding the user's performance (e.g., sports performance), noise reduction and/or cancellation, hydration detection for prolonged EMG sensor longevity, and user identification.

The wearable device can include a wristband or strap that can incorporate one or more sensors capable of determining the axial orientation of the user's wrist and/or capable of detecting changes in the position of the wearer's wrist. In some examples, the sensors can include

DETAILED DESCRIPTION

Figure 1:
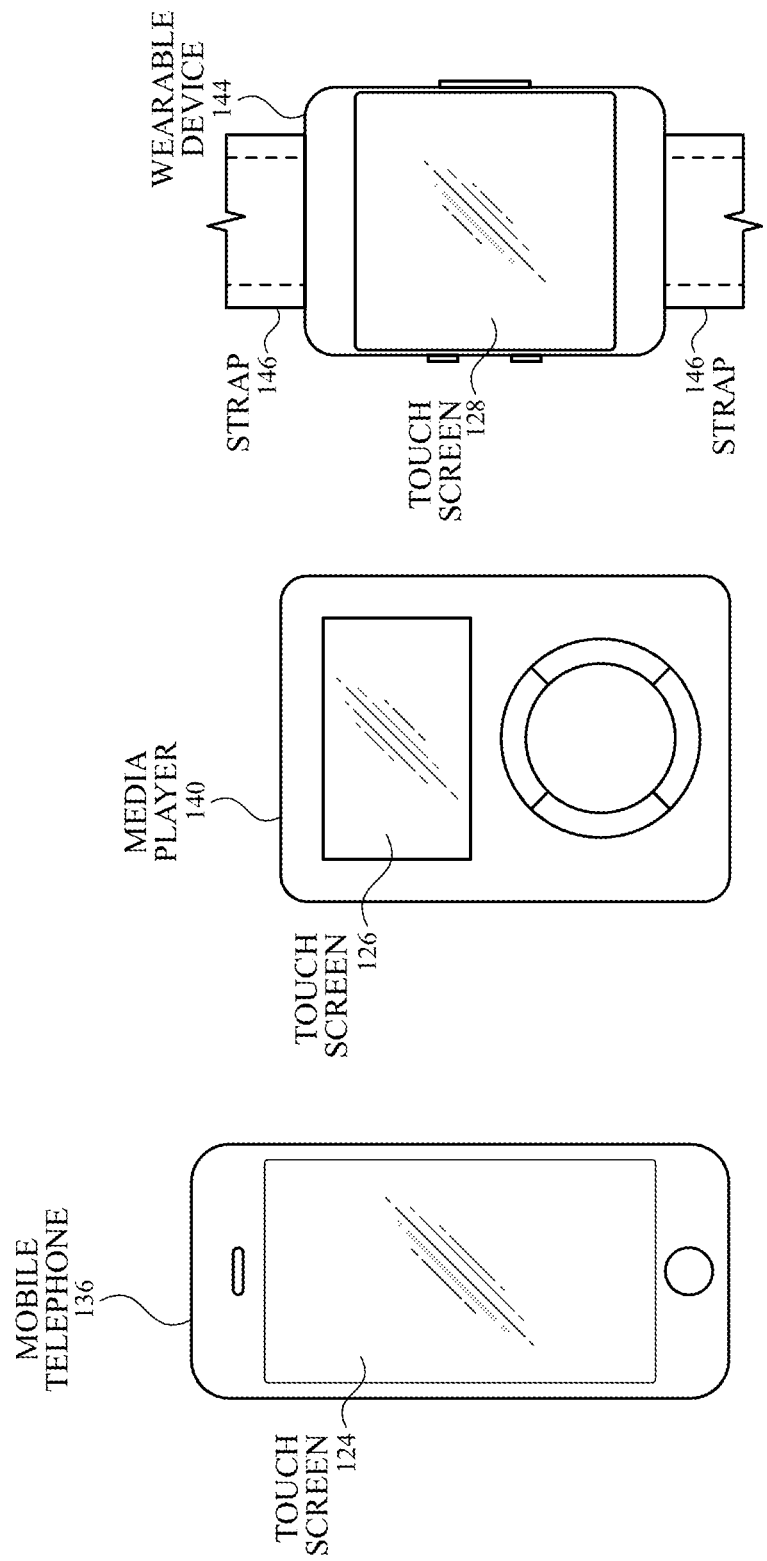
FIGS. 1A-1C illustrate systems in which examples of the disclosure can be implemented

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

This relates to systems and methods for determining the axial orientation and location of the user's wrist. The axial orientation and location can be determined using one or more sensors located on the strap, the device underbody, or both. For example, the strap (attached to the device underbody) can include a plurality of elastic sections and a plurality of rigid sections. Each elastic section can include one or more flex sensors. The flex sensors can be sensors configured to generate one or more signals indicative of the expansion or contractions of the user's wrist due to extension or tension, for example. In some examples, on or more electromyography (EMG) sensors can be included to measure the user's electrical signals, and the user's muscle activity can be determined. Measurements from the EMG sensors can be used in conjunction with one or more other sensor measurements, such as PPG sensor measurements, to determine one or more user characteristics. In some examples, a plurality of strain gauges (e.g., piezoelectric sensors) can be included to generate one or more signals indicative of any changes in shape, size, and/or physical properties of the user's wrist. In some examples, the device can include a plurality of capacitance sensors for increased granularity and/or sensitivity in measuring the amount of tension exerted by the user's wrist. The systems and methods disclosed can include analysis and feedback to a user regarding the user's performance (e.g., sports performance), noise reduction and/or cancellation, hydration detection for prolonged EMG sensor longevity, and user identification.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the systems and methods for determining axial orientation of the user's wrist, as will be disclosed.

Figure 2:
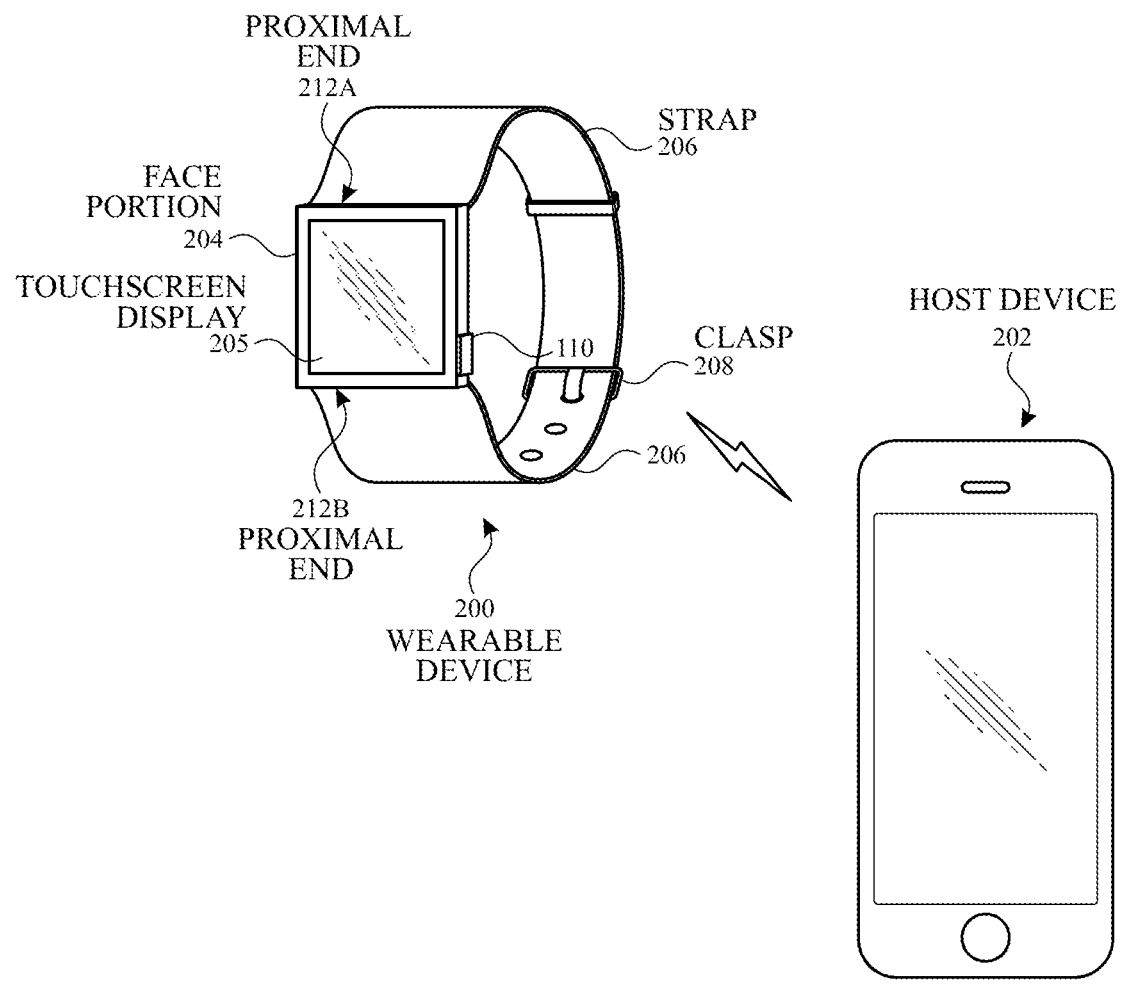
FIG. 2 illustrates an exemplary wearable device communicating wirelessly with a host device according to examples of the disclosure.

FIG. 2 illustrates an exemplary wearable device communicating wirelessly with a host device according to examples of the disclosure. Wearable device 200 can be a wristwatch-like device with face portion 204 connected to strap 206. Face portion 204 can include, for example, a touchscreen display 205 that can be appropriately sized depending on where wearable device 200 is intended to be worn. The user can view information presented by wearable device 200 on touchscreen display 205 and can provide input to wearable device 200 by touching touchscreen display 205. In some examples, touchscreen display 205 can occupy most or all of the front surface of face portion 204.

Strap 206 (also referred to herein as a wristband or wrist strap) can be provided to allow device 200 to be removably worn (e.g., around the user's wrist) by the user. In some examples, strap 206 can include a flexible material (e.g., fabrics, flexible plastics, leather, chain links, or flexibly interleaved plates or links made of metal or other rigid materials) and can be connected to face portion 204 (e.g., by hinges, loops, or other suitable attachment devices or holders). In some examples, strap 206 can be made of two or more sections of a rigid material joined by clasp 208. One or more hinges can be positioned at the junction of face 204 and proximal ends 212A and 212B of strap 206 and/or elsewhere along the lengths of strap 206 (e.g., to allow a user to put on and take off wearable device 200). Different portions of strap 206 can include different materials. For example, strap 206 can include flexible or expandable sections alternating with rigid sections. In some examples, strap 206 can include removable sections, allowing wearable device 200 to be resized to accommodate a particular user's wrist size. In some examples, strap 206 can include portions of a continuous strap member that runs behind or through face portion 204. Face portion 204 can be detachable from strap 206, permanently attached to strap 206, or integrally formed with strap 206.

In some examples, strap 206 can include clasp 208 that can facilitate with connection and disconnection of distal ends of strap 206. In some examples, clasp 208 can include buckles, magnetic clasps, mechanical clasps, snap closures, etc. In some examples, wearable device 200 can be resized to accommodate a particular user's wrist size. Accordingly, device 200 can be secured to a user's person (e.g., around the user's wrist) by engaging clasp 208. Clasp 208 can be subsequently disengaged to facilitate removal of device 200 from the user's person.

In some examples, strap 206 can be formed as a continuous band of an elastic material (including, for example, elastic fabrics, expandable metal links, or a combination of elastic and inelastic sections), allowing wearable device 200 to be put on and taken off by stretching a band formed by strap 206 connecting to face portion 204. Thus, clasp 208 may not be required.

Strap 206 (including any clasp that may be present) can include one or more sensors that can allow wearable device 200 to determine whether the device is worn by the user at any given time. Wearable device can operate differently depending on whether the device is currently being worn or not. For example, wearable device 200 can inactivate various user interface and/or RF interface components when it is not being worn. In addition, in some examples, wearable device 200 can notify host device 202 when a user puts on or takes off wearable device 200. Further, strap 206 can include sensors capable of detecting wrist articulations of a user.

Host device 202 can be any device that can communicate with wearable device 200. Although host device 202 is illustrated in the figure as a smart phone, examples of the disclosure can include other devices, such as a tablet computer, a media player, any type of mobile device, a laptop or desktop computer, or the like. Other examples of host devices can include point-of-sale terminals, security systems, environmental control systems, and so on. Host device 202 can communicate wirelessly with wearable device 200 using, for example, protocols such as Bluetooth or Wi-Fi. In some examples, wearable device 200 can include electrical connector 210 that can be used to provide a wired connection to host device 202 and/or to other devices (e.g., by using suitable cables). For example, connector 210 can be used to connect to a power supply to charge an onboard battery of wearable device 200.

In some examples, wearable device 200 and host device 202 can interoperate to enhance functionality available on host device 202. For example, wearable device 200 and host device 202 can establish a pairing using a wireless communication technology, such as Bluetooth. While the devices are paired, host device 202 can send notifications of selected events (e.g., receiving a phone call, text message, or email message) to wearable device 200, and wearable device 200 can present corresponding alerts to the user. Wearable device 200 can also provide an input interface via which a user can respond to an alert (e.g., to answer a phone call or reply to a text message). In some examples, wearable device 200 can also provide a user interface that can allow a user to initiate an action on host device 202, such as unlocking host device 202 or turning on its display screen, placing a phone call, sending a text message, or controlling media playback operations of host device 202. Techniques described herein can be adapted to allow a wide range of host device functions to be enhanced by providing an interface via wearable device 200.

It will be appreciated that wearable device 200 and host device 202 are illustrative and that variations and modifications are possible. For example, wearable device 200 can be implemented in a variety of wearable articles, including a watch, a bracelet, or the like. In some examples, wearable device 200 can be operative regardless of whether host device 202 is in communication with wearable device 200; a separate host device may not be required.

Figure 3:
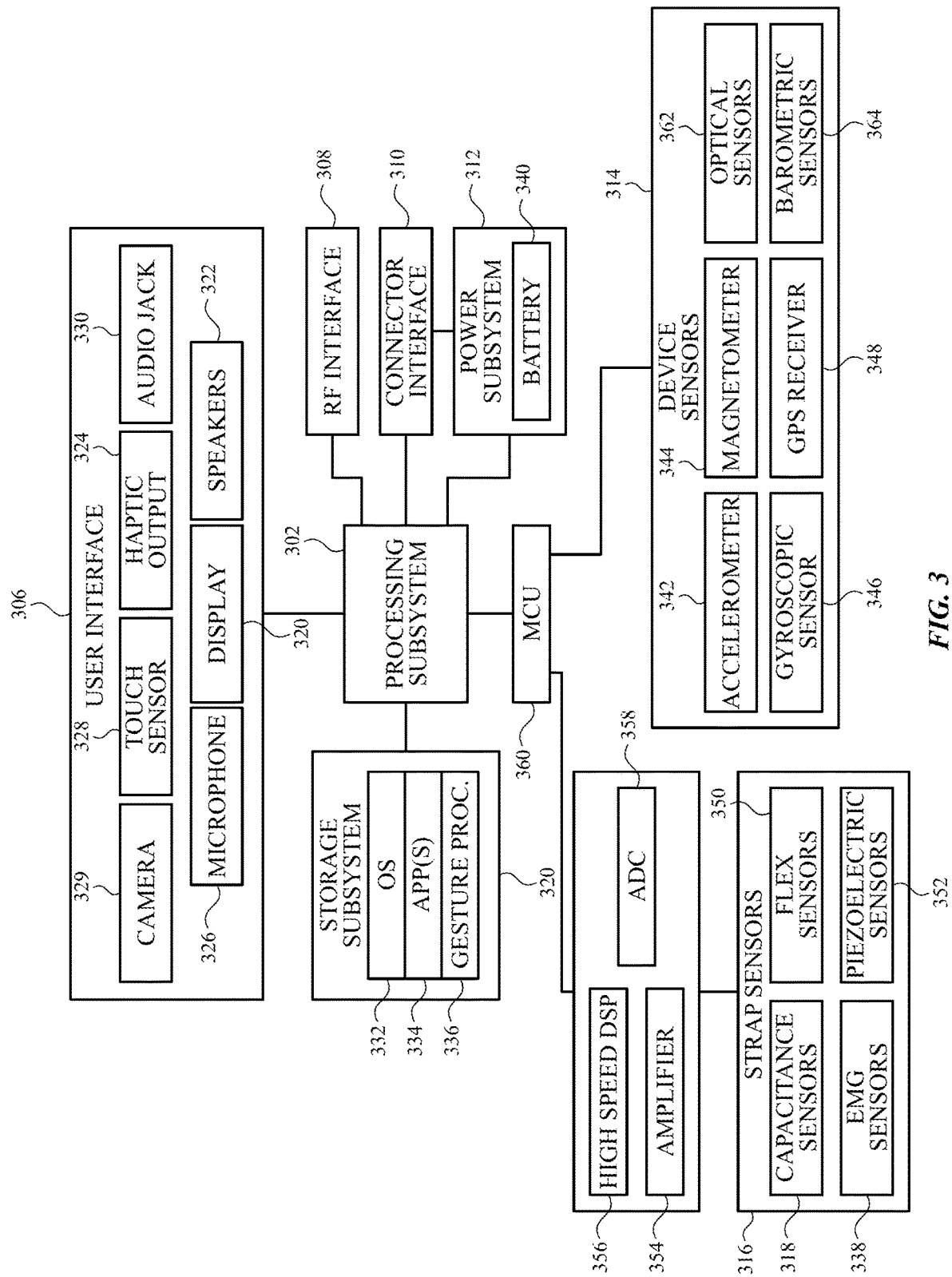
FIG. 3 illustrates a block diagram of an exemplary wearable device according to examples of the disclosure.

Wearable device 200 can be implemented using electronic components disposed within face portion 204 and/or strap 206. FIG. 3 illustrates a block diagram of an exemplary wearable device according to examples of the disclosure. Wearable device 300 can include processing subsystem 302, storage subsystem 304, user interface 306, RF interface 308, connector interface 310, power subsystem 312, device sensors 314, and strap sensors 316. Wearable device 300 can also include other components (not explicitly shown)

Storage subsystem 304 can be implemented using, for example, magnetic storage media, flash memory, other semiconductor memory (e.g., DRAM, SRAM), or any other non-transitory storage medium, or a combination of media, and can include volatile and/or non-volatile media. In some examples, storage subsystem 304 can store media items such as audio files, video files, image or artwork files; information from a user's contacts (e.g., names, addresses, phone numbers, etc.); information about a user's scheduled appointments and events; notes; and/or other types of information. In some examples, storage subsystem 304 can also store one or more application programs (or apps) 334 to be executed by processing subsystem 302 (e.g., video game programs, personal information management programs, media playback programs, interface programs associated with particular host devices, and/or host device functionalities, etc.).

User interface 306 can include any combination of input and output devices. A user can operate input devices of user interface 306 to invoke the functionality of wearable device 300 and can view, hear, and/or otherwise experience output from wearable device 300 via output devices of user interface 306.

Examples of output devices can include display 320, speakers 322, and haptic output generator 324. Display 320 can be implemented using compact display technologies (e.g., liquid crystal display (LCD), light-emitting diodes (LEDs), organic light-emitting diodes (OLEDs), or the like). In some examples, display 320 can incorporate a flexible display element or curved-glass display element, allowing wearable device 300 to conform to a desired shape. One or more speakers 322 can be provided using small-form-factor speaker technologies, including any technology capable of converting electronic signals into audible sound waves. In some examples, speakers 322 can be used to produce tones (e.g., beeping or ringing) and can but need not be capable of reproducing sounds such as speech or music with any particular degree of fidelity. Haptic output generator 324 can be, for example, a device that can convert electronic signals into vibrations. In some examples, the vibrations can be strong enough to be felt by a user wearing wearable device 300, but not so strong as to produce distinct sounds.

Examples of input devices can include microphone 326, touch sensor 328, and camera 329. Microphone 326 can include any device that converts sound waves into electronic signals. In some examples, microphone 326 can be sufficiently sensitive to provide a representation of specific words spoken by a user. In some examples, microphone 326 can be usable to provide indications of general ambient sound levels without necessarily providing a high-quality electronic representation of specific sounds.

Touch sensor 328 can include, for example, a capacitive sensor array with the ability to localize contacts to a particular point(s) or region on the surface of the sensor. In some examples, touch sensor 328 can distinguish multiple simultaneous contacts. In some examples, touch sensor 328 can be overlaid over display 320 to provide a touchscreen interface (e.g., touchscreen interface 205 of FIG. 2), and processing subsystem 302 can translate touch events (including taps and/or other gestures made with one or more contacts) into specific user inputs depending on what is currently displayed on display 320.

Camera 329 can include, for example, a compact digital camera that includes an image sensor such as a CMOS sensor and optical components (e.g., lenses) arranged to focus an image onto the image sensor, along with control logic operable to use the imaging components to capture and store still and/or video images. Images can be stored, for example, in storage subsystem 304 and/or transmitted by wearable device 300 to other devices for storage. Depending on implementation, the optical components can provide fixed focal distance or variable focal distance. In some examples, with variable focal distance, autofocus can be provided. In some examples, camera 329 can be disposed along an edge of the face member (e.g., top edge of face portion 204 of FIG. 2) and oriented to allow a user to capture images of nearby objects in the environment, such as a bar code or QR code. In some examples, camera 329 can be disposed on the front surface of face portion 204 (e.g., to capture images of the user). Any number of cameras can be provided, depending on the implementation.

In some examples, user interface 306 can provide output to and/or receive input from an auxiliary device, such as a headset. For example, audio jack 330 can connect via an audio cable (e.g., a standard 2.5-mm or 3.5-mm audio cable) to an auxiliary device. Audio jack 330 can include input and/or output paths. Accordingly, audio jack 330 can provide audio to and/or receive audio from the auxiliary device. In some examples, a wireless connection interface can be used to communicate with an auxiliary device.

Processing subsystem 302 can be implemented as one or more integrated circuits (e.g., one or more single-core or multi-core microprocessors or microcontrollers). In operation, processing system 302 can control the operation of wearable device 300. In some examples, processing subsystem 302 can execute a variety of programs in response to program code and can maintain multiple concurrently executing programs or processes. At any given time, some or all of the program code to be executed can be stored in processing subsystem 302 and/or in storage media such as storage subsystem 304.

Through suitable programming, processing subsystem 302 can provide various functionality for wearable device 300. For example, processing subsystem 302 can execute an operating system (OS) 332 and various applications 334 such as a phone-interface application, a text-message-interface application, a media interface application, a fitness application, and/or other applications. In some examples, some or all of these application programs can interface with a host device, for example, by generating messages to be sent to the host device and/or by receiving and interpreting messages from the host device. In some examples, some or all of the application programs can operate locally to wearable device 300. For example, if wearable device 300 has a local media library stored in storage subsystem 304, a media interface application can provide a user interface to select and play locally stored media items. Processing subsystem 302 can also provide wrist-gesture-based control, for example, by executing gesture processing code 335 (which can be part of OS 323 or provided separately as desired).

RF (radio frequency) interface 308 can allow wearable device 300 to communicate wirelessly with various host devices. RF interface 308 can include RF transceiver components, such as an antenna and supporting circuitry, to enable data communication over a wireless medium (e.g., using Wi-Fi/IEEE 802.11 family standards), Bluetooth, or other protocols for wireless data communication. RF interface 308 can be implemented using a combination of hardware (e.g., driver circuits, antennas, modulators/demodulators, encoders/decoders, and other analog and/or digital signal processing circuits) and software components. In some examples, RF interface 308 can provide near-field communication ("NFC") capability (e.g., implementing the ISO/IEC 18092 standards or the like). In some examples, NFC can support wireless data exchange between devices over a very short range (e.g., 20 cm or less). Multiple different wireless communication protocols and associated hardware can be incorporated into RF interface 308.

Connector interface 310 can allow wearable device 300 to communicate with various host devices via a wired communication path, for example, using Universal Serial Bus (USB), universal asynchronous receiver/transmitter (UART), or other protocols for wired data communication. In some examples, connector interface 310 can provide a power port, allowing wearable device 300 to receive power, for example, to charge battery 340. For example, connector interface 310 can include a connector such as a mini-USB connector or a custom connector, as well as supporting circuitry. In some examples, the connector can be a custom connector that can provide dedicated power and ground contacts, as well as digital data contacts that can be used to implement different communication technologies in parallel. For example, two pins can be assigned as USB data pins (D+ and D−) and two other pins can be assigned as serial transmit/receive pins (e.g., implementing a UART interface). The assignment of pins to particular communication technologies can be hardware or negotiated while the connection is being established. In some examples, the connector can also provide connections for audio and/or video signals, which can be transmitted to or from host device 302 in analog and/or digital formats.

In some examples, connector interface 310 and/or RF interface 308 can be used to support synchronization operations in which data can be transferred from a host device to wearable device 300 (or vice versa). For example, as described below, a user can customize certain information for wearable device 300 (e.g., settings related to wrist-gesture control). While user interface 306 can support data-entry operations, a user may find it more convenient to define customized information on a separate device (e.g., a tablet or smartphone) that can have a larger interface (e.g., including a real or virtual alphanumeric keyboard). The customized information can be transferred to wearable device via a synchronization operation. Synchronization operations can also be used to load and/or update other types of data in storage subsystem 304, such as media items, application programs, personal data, and/or operating system programs. Synchronization operations can be performed in response to an explicit user request and/or automatically (e.g., when wearable device 200 resumes communication with a particular host device or in response to either device receiving an update to its copy of synchronized information).

Device sensors 314 can include various electronic, mechanical, electromechanical, optical, and/or other apparatus that can provide information related to external conditions around wearable device 300. Sensors 314 can provide digital signals to processing subsystem 303, for example, on a streaming basis or in response to polling by process subsystem 302 as desired. Any type and combination of device sensors can be used. For example, device sensors 314 can include accelerometer 342, magnetometer 344, gyroscopic sensor 346, GPS (global positioning system) receiver 348, optical sensors 362, and barometric sensors 364. One or more of device sensors 314 can provide information about the location and/or motion of wearable device 300. For example, accelerometer 342 can sense acceleration (e.g., relative to freefall) along one or more axes, for example, using piezoelectric or other components in conjunction with associated electronics to produce a signal. Magnetometer 344 can sense an ambient magnetic field (e.g., Earth's magnetic field) and can generate a corresponding electrical signal, which can be interpreted as a compass direction. Gyroscopic sensor 346 can sense rotational motion in one or more directions, for example, using one or more micro-electro-mechanical systems (MEMS) gyroscopes and related control and sense circuitry. GPS receiver 348 can determine location based on signals received from GPS satellites. Optical sensors 362 can sense one or optical properties of light used, for examples, in determining photoplethsmyogram (PPG) information associated with the user. In some examples, optical sensors 362 can include ambient light sensors (ALS) to determine ambient light properties. Barometric sensors 364 can sense the atmospheric pressure to resolve vertical location information of the device.

Other sensors can also be included in addition to, or instead of, these examples. For example, a sound sensor can incorporate microphone 326 together with associated circuitry and/or program code to determine, for example, a decibel level of ambient sound. Temperature sensors, proximity sensors, ultrasound sensors, or the like can also be included.

Strap sensors 316 can include various electronic, mechanical, electromechanical, optical, or other devices that can provide information as to whether wearable device 300 is currently being worn, as well as information about forces that may be acting on the strap due to movement of the user's wrist. Examples of strap sensors 316 are described below. In some examples, signals from strap sensors 316 can be analyzed, for example, using gesture processing code 336 to identify wrist gestures based on the sensor signals. Such gestures can be used to control operations of wearable device 300.

Power subsystem 312 can provide power and power management capabilities for wearable device 300. For example, power subsystem 312 can include battery 340 (e.g., a rechargeable battery) and associated circuitry to distribute power from battery 340 to other components of wearable device 300 that can require electrical power. In some examples, power subsystem 312 can also include circuitry operable to charge battery 340, for example, when connector interface 310 can be connected to a power source. In some examples, power subsystem can include a "wireless" charger, such as an inductive charger, to charge battery 340 without relying on connector interface 310. In some examples, power subsystem 312 can also include other power sources (e.g., solar cell) in addition to, or instead of, battery 340.

In some examples, power subsystem 312 can control power distribution to components within wearable device 300 to manage power consumption efficiently. For example, power subsystem 312 can automatically place device 300 into a "hibernation" (or sleep/inactive) state when strap sensors 316 or other sensors indicate that device 300 is not being worn by the user. The hibernation state can be designed to reduce power consumption. For example, user interface 306 (or components thereof), RF interface 308, connector interface 310, and/or device sensors 314 can be powered down (e.g., to a low-power state or turned off entirely), while strap sensors 316 can be powered up (either continuously or at intervals) to detect when a user puts on wearable device 300. In some examples, while wearable device 300 is being worn, power subsystem 312 can turn display 320 and/or other components on or off depending on motion and/or orientation of wearable device 300 detected by device sensors 314. For instance, if wearable device 300 can be designed to be worn on a user's wrist, power subsystem 312 can detect raising and rolling of the user's wrist, as is typically associated with looking at the face of a wristwatch based on information provided by accelerometer 342. In response to this detected motion, power subsystem 312 can automatically turn display 320 and/or touch sensor 328 on. Similarly, power subsystem 312 can automatically turn display 320 and/or touch sensor 328 off in response to detecting that the user's wrist has returned to a neutral position (e.g., hanging down). As discussed below, in some examples, other sensors can be used to determine the axial orientation of the user's wrist for waking up (e.g., switching from an inactive state to an active state with higher power consumption) the wearable device or putting the device into a hibernation state.

Power subsystem 312 can also provide other power management capabilities, such as regulating power consumption of other components of wearable device 300 based on the source and amount of available power, monitoring and stored power in battery 340, generating user alerts if the stored power drops below a minimum level, etc.

In some examples, control functions of power subsystem 312 can be implemented using programmable or controllable circuits operating in response to control signals generated by processing subsystem 302 in response to program code executing thereon, or as a separate microprocessor or microcontroller.

Examples of the disclosure can include variations and modifications to the block diagram illustrated in FIG. 3. For example, strap sensors 316 can be modified, and wearable device 300 can include a user-operable control (e.g., a button or switch) that the user can operate to provide input. Controls can also be provided, for example, to turn on or off display 320, mute or unmute sounds from speakers 322, etc. Wearable device 300 can include any types and combination of sensors, and in some examples, can include multiple sensors of a given type.

In some example, a user interface can include any combination of any or all of the components described above, as well as other components not expressly described. For example, the user interface can include just a touch screen, or a touchscreen and a speaker, or a touchscreen and a haptic device. Where the wearable device includes a RF interface, a connector interface can be omitted, and all communication between the wearable device and other devices can be conducted using wireless communication protocols. A wired power connection (e.g., for charging a battery of the wearable device) can be provided separately for any data connection.

Further, while the wearable device is described with reference to functional blocks, it is to be understood that these blocks are defined for convenience of description and are not intended to imply a particular physical arrangement of component parts. Further, the blocks need not correspond to physically distinct components. Blocks can be configured to perform various operations (e.g., by programming a processor or providing appropriate control circuitry), and various blocks might or might not be reconfigurable depending on how the initial configuration is obtained. Examples of the disclosure can be realized in a variety of apparatuses including electronic devices implemented using any combination of circuitry and software. Furthermore, examples of the disclosure are not limited to requiring every block illustrated in the figure to be implemented in a given wearable device.

A host device (e.g., host device 202 of FIG. 2) can be implemented as an electronic device using blocks similar to those described above (e.g., processors, storage media, user interface devices, data communication interfaces, etc.) and/or other blocks or components. Any electronic device capable of communicating with a particular wearable device can act as a host device with respect to that wearable device. Communication between a host device and a wireless device can be implemented according to any communication protocol (or combination of protocols) that both devices can be programmed or otherwise configured to use. In some examples, such protocols (e.g., Bluetooth) can be used. In some examples, a custom message format and syntax (including, for example, a set of rules for interpreting particular bytes or sequences of bytes in a digital data transmission) can be defined, and messages can be transmitted using standard serial protocols (e.g., a virtual serial port defined in certain Bluetooth standards).

Figure 4A:
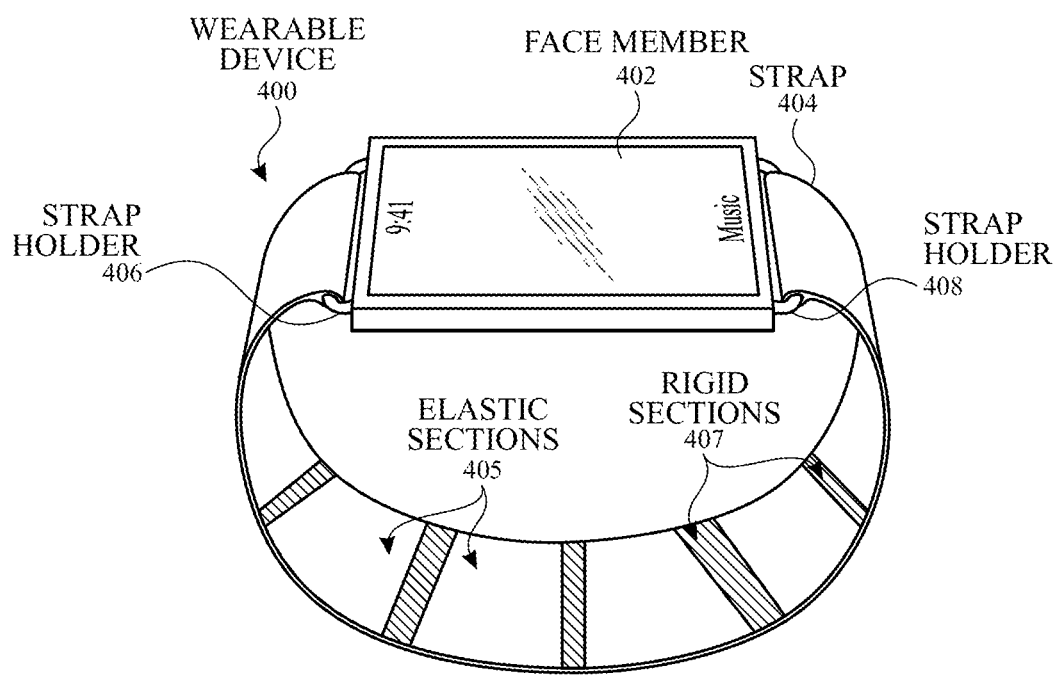
FIG. 4A illustrates a perspective view of an exemplary wearable device having a strap that can include a plurality of elastic sections and a plurality of rigid sections according to examples of the disclosure.

Examples of the disclosure can include systems and methods that can assist the user with determining and evaluating information related to the user's wrist. In some examples, the exemplary wearable device can be capable of measuring the amount of tension in the user's wrist. FIG. 4A illustrates a perspective view of an exemplary wearable device having a strap that can include a plurality of elastic sections and a plurality of rigid sections according to examples of the disclosure. Wearable device 400 can include face member 402 and strap 404. Strap 404 can be connected to face member 402 using strap holders 406 and 408 disposed along top and bottom sides of face member 402. In some examples, strap holders 406 and 408 can be expandable strap holders.

In some examples, strap 404 can include a plurality of elastic sections 405 interleaved with a plurality of rigid sections 407. Each elastic section 405 can include one or more flex sensors (e.g., flex sensor 350 illustrated in FIG. 3). The flex sensors can be sensors configured to expand when the user's wrist extends, for example. In some example, the flex sensors can be configured to contract when the user's wrist has more tension. The flex sensors can include an elastic material (e.g., elastic strap) or can include at least a partially embedded material. An electrical resistance can be measured across strap 404, the flex sensors, elastic section(s), and/or the partially embedded material. When strap 404 expands, an increase in electrical resistance can be measured; when strap 404 contracts, a decrease in electrical resistance can be measured.

Figure 4B:
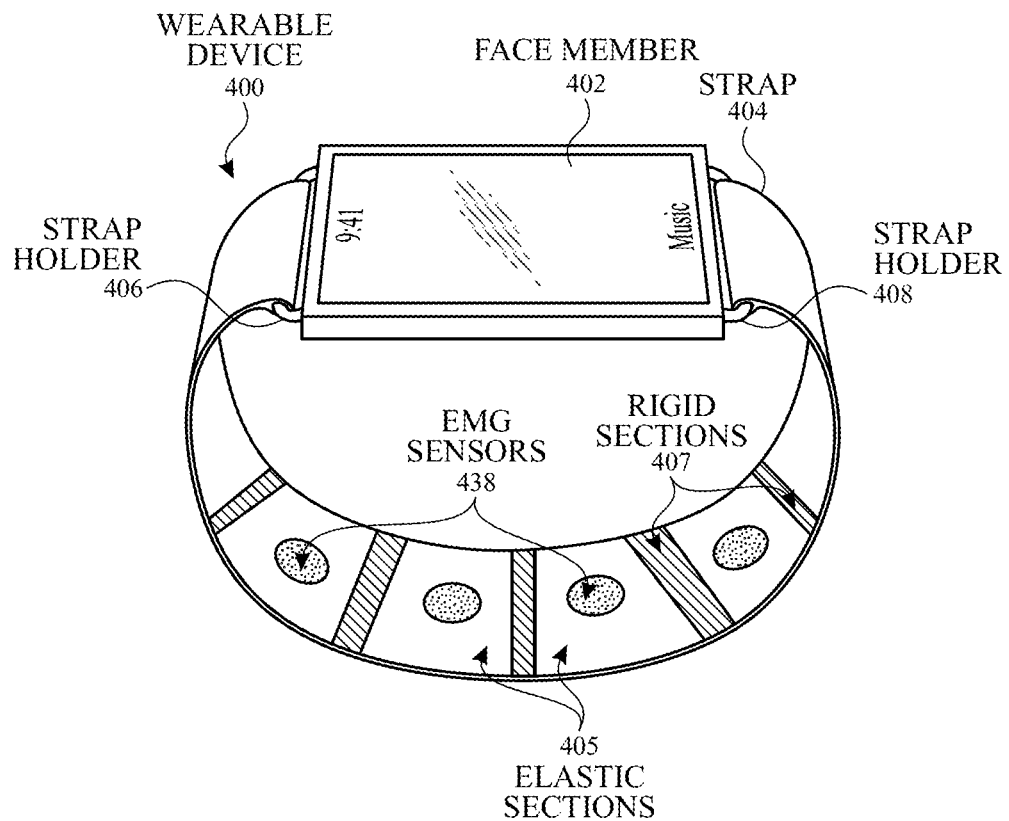
FIG. 4B illustrates a perspective view of an exemplary wearable device having a strap including one or more electrodes embedded at least partially within one or more elastic sections according to examples of the disclosure.

In some examples, elastic sections 405 can include one or more electrodes embedded at least partially within the elastic section, as illustrated in FIG. 4B. Electrodes 438 can be configured as electromyography (EMG) sensors, which can sense muscle activity by measuring electrical activity. In some examples, electrodes 438 can be disposed on elastic section 405 such that an exposed surface of electrodes 438 can contact the user's wrist (e.g., contacting the inner side of strap 404). In this manner, one elastic section 405 can be coupled to multiple measurement types, such as strain and EMG signals.

Measurements from the EMG sensors can be used in conjunction with one or more other sensor measurements, such as PPG sensor measurements, to determine one or more user characteristics. For example, the device can be configured to determine the user's calorimetric expenditure using the determined muscle activity (related to the electrical activity measured using the EMG sensors) and the determined user's heart rate (related to the blood oxygen activity measured using the PPG sensors).

Figure 4C:
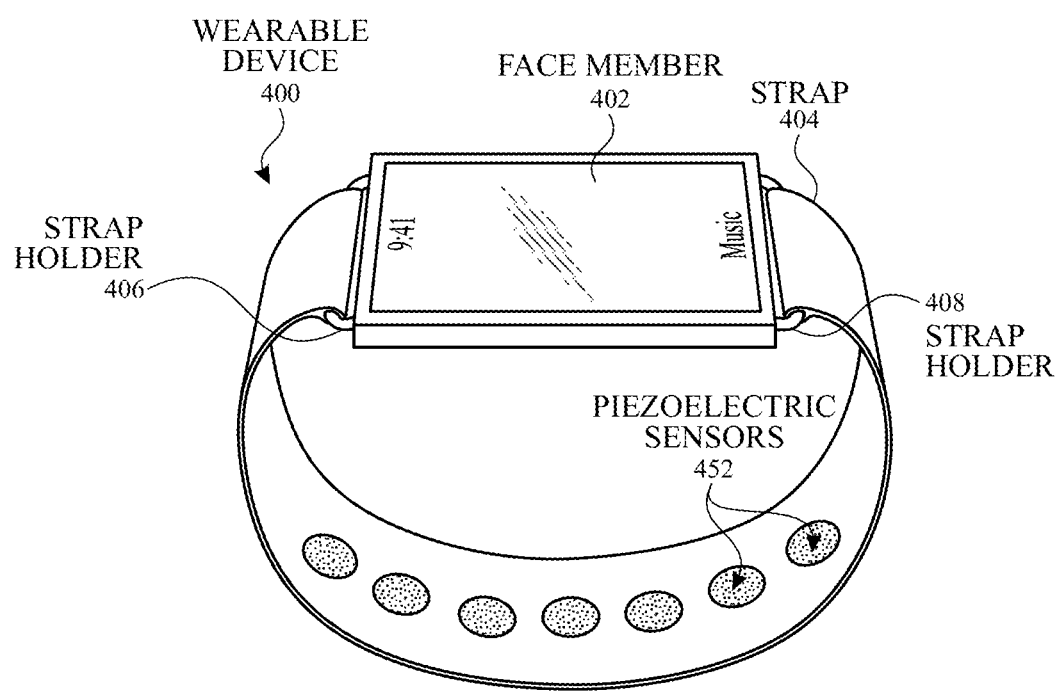
FIG. 4C illustrates a perspective view of an exemplary wearable device having a strap that can include strain gauge sensors according to examples of the disclosure.

In some examples, strap 404 can include a plurality of strain gauges, as illustrated in FIG. 4C. The plurality of strain gauges can include, for example, piezoelectric sensors 452. Strap 404 can be secured around at least a portion of the user's wrist. When the user's wrist moves, one or more materials included in piezoelectric sensors 452 can change shape (e.g., deform) and/or any physical properties, and a signal (e.g., voltage) proportional to the change in shape can be generated. In some examples, each of the piezoelectric sensors 452 can be independently controlled, which can give the device capability of determining the location of the tension.

Coupled with the signals(s) indicative of the amount of tension, one or more strain "images" of the user's wrist can be generated. The strain image can be a two dimensional representation of the location and intensity of tension. The strain image (or information from the strain gauges) can be used at least in part to determine axial orientation of the wearable device on the user's wrist. For example, when a user grips his or her hand, the bottom side (e.g., palm side) of the user's wrist can experience larger movement due to the tendons undergoing movement and being located closer to the bottom side. One or more strain gauges that experience greater strain (e.g., higher measured voltage) can be associated with the location(s) of the user's tendon(s). From this association, the axial orientation of the device can be determined.

Figure 5:
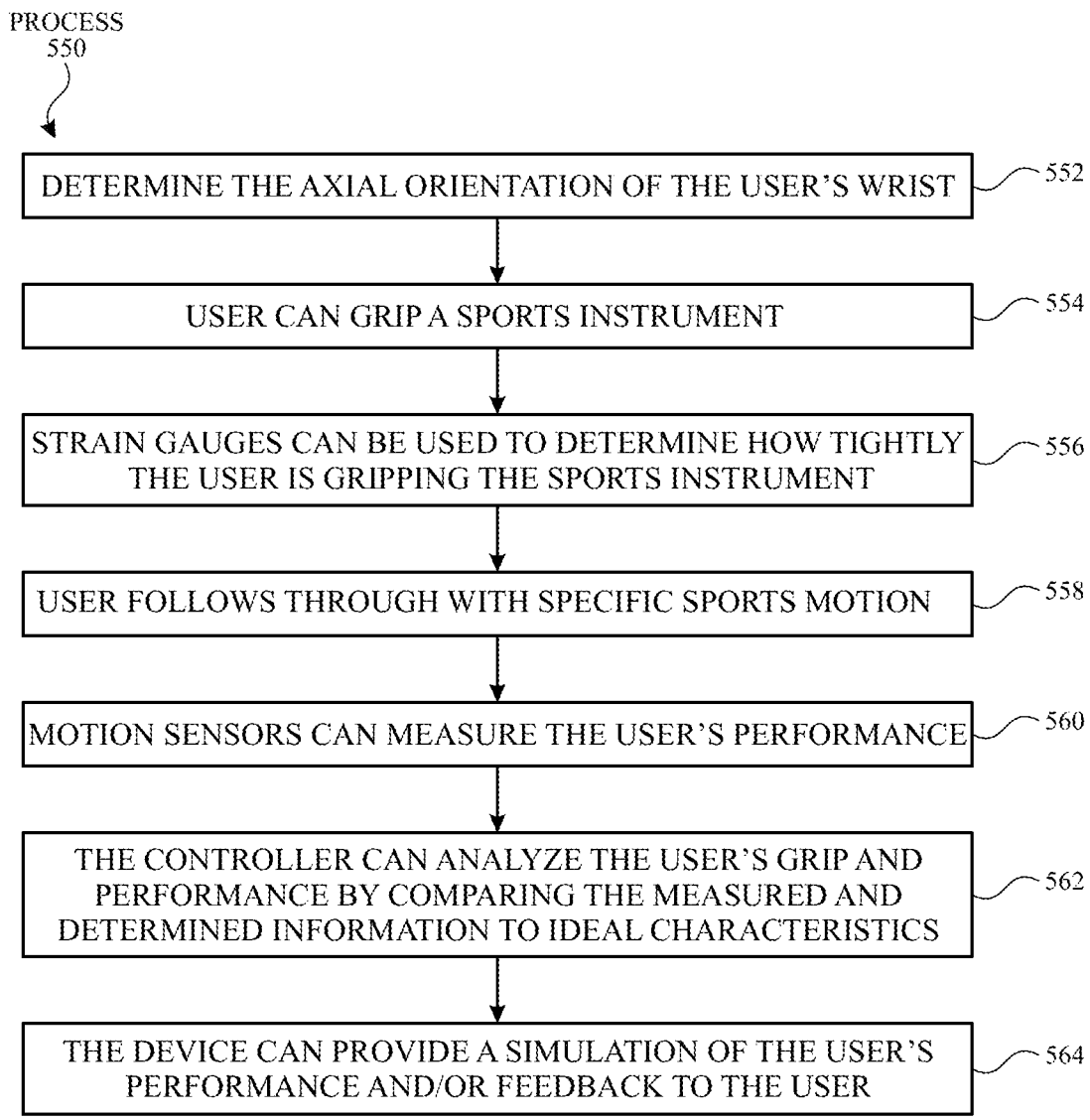
FIG. 5 illustrates an exemplary method for providing analysis and feedback to a user regarding the user's sports performance according to examples of the disclosure.

In some examples, the strain gauges can be coupled with one or more other types of sensors to provide analysis and user feedback. FIG. 5 illustrates an exemplary method for providing analysis and feedback to a user regarding the user's performance according to examples of the disclosure. The device can determine the axial orientation on the user's wrist (step 552 of process 550). The user can grip an instrument. In some examples, the instrument can be a sports instrument (e.g., golf club, baseball bat, etc.)(step 554 of process 550). The strain gauges can be used to determine how tightly the user is gripping the sports instrument (step 556 of process 550). The user may then proceed to follow through with a specific sports motion (e.g., swinging the golf club or throwing a football) (step 558 of process 550). The motion sensors (e.g., accelerometer 342 or barometric sensors 364 of FIG. 3) can measure the user's performance in terms of, for example, acceleration, trajectory of the sports instrument, etc. (step 560 of process 550). The device's controller can analyze the user's grip and performance by comparing the measured and determined information to ideal characteristics (e.g., stored in memory), for example (step 562 of process 550). From the comparison, the device can provide a simulation of the user's performance and/or feedback to the user on how to improve (step 564 of process 550).

Although FIG. 5 illustrates an exemplary method for analysis of sports performance, examples of the disclosure can include analysis and feedback for any type of user motion including gross motion (e.g., the user brushing his or her hair) and fine motor motion (e.g., the user typing on a keyboard). In some examples, if the user is moving or stirring more than a predetermined amount or if the user's tension is greater than a predetermined amount, the strain gauges may be perturbed and measurements from the strain gauges may be inaccurate. One or more EMG sensors can be configured to measure the tension of the user's wrist. Additionally, although FIG. 5 is discussed in the context of strain gauges used to determine the axial orientation, examples of the disclosure can include other types of sensors, such as capacitive sensors discussed below.

Figure 6:
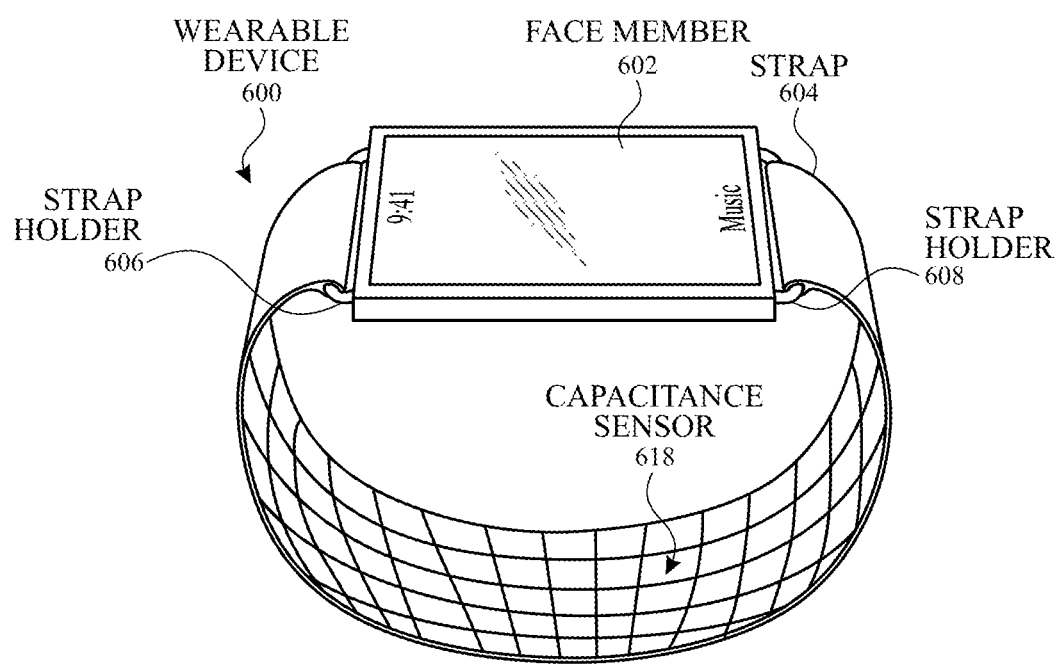
FIG. 6 illustrates a perspective view of an exemplary wearable device having a strap that can include capacitive sensors according to examples of the disclosure.

In some examples, the exemplary wearable device can be capable of measuring the amount of tension with increased granularity and/or sensitivity. FIG. 6 illustrates a perspective view of an exemplary wearable device having a strap that can include capacitive sensors according to examples of the disclosure. Wearable device 600 can include face member 602 and strap 604. Strap 604 can be connected to face member 602 using strap holders 606 and 608 disposed along top and bottom sides of face member 602.

Strap 604 can include a plurality of capacitance sensors 618. Plurality of capacitance sensors 618 can be located on the inner side (i.e., side facing the underbody of the wearable device body) of strap 604. In some examples, plurality of capacitance sensors 618 can also be located at least partially on the outer side of strap 604. Plurality of capacitance sensors 618 can be configured to sense one or more changes in capacitance due to, for example, the increased (or decreased) capacitive coupling as the user's wrist applies force to the electrodes. One or more capacitance "images" of the user's wrist can be generated. The capacitance image can be a two-dimensional representation of the location and/or intensity of applied force. In some examples, plurality of capacitance sensors 618 can include a grid (e.g., drive lines and sense lines arranged in rows and columns) of electrodes.

In some examples, strap holders 606 and 608 can include one or more electrical connections for transmitting signals from the one or more sensors (e.g., capacitance sensors 618) to the body (e.g., including face member 602) of the wearable device. In some examples, some of the capacitance sensors and/or other sensors (e.g., optical sensors) can be configured to couple (e.g., capacitively couple) to one or more sensors included in the body. A processor or controller can be configured utilize the coupling to transmit the signal(s) from the sensors included in strap 704 to the body of wearable device 600.

Figure 7A:
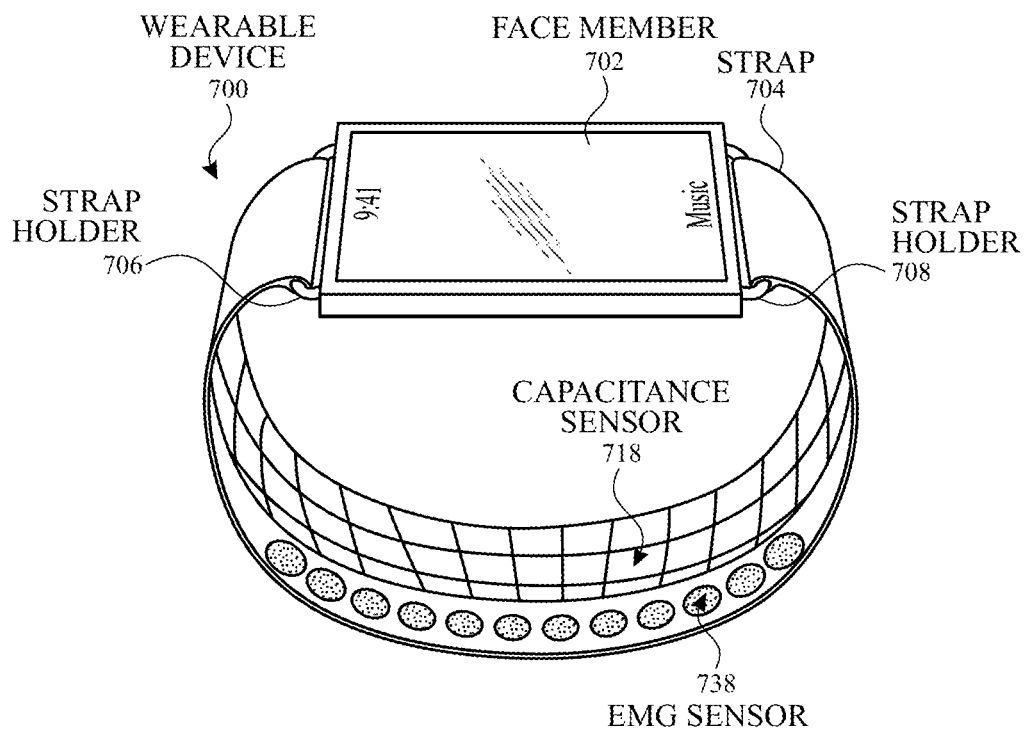
FIG. 7A illustrates a perspective view of an exemplary wearable device having a strap that can include capacitive and EMG sensors according to examples of the disclosure.

FIG. 7A illustrates an exemplary wearable device having a strap that can include EMG and capacitive sensors according to examples of the disclosure. Wearable device 700 can include face member 702 and strap 704. Strap 704 can be connected to face member 702 using strap holders 706 and 708 disposed along top and bottom sides of face member 702. In some examples, strap holders 706 and 708 can be expandable strap holders.

Strap 704 can also include EMG sensors 738 and/or capacitance sensors 718. EMG sensors 738 can include one or more electrodes configured to measure electrical activity. One or more signals indicative of the measured electrical activity can be generated, and the user's muscle activity can be determined from the signal(s). An exposed surface of EMG sensors 738 can contact the user's wrist (e.g., contacting the inner side of strap 704).

Capacitance sensors 718 can also be located on the inner side (i.e., side facing the underbody of the wearable device body) of strap 704. In some examples, plurality of capacitance sensors 718 can also be located at least partially on the outer side of strap 704. Plurality of capacitance sensors 718 can be configured to sense one or more changes in capacitance due to, for example, the increased (or decreased) capacitive coupling as the user's wrist applies force to the electrodes. One or more capacitance "images" of the user's wrist can be generated. The capacitance image can be a two dimensional representation of the location and/or intensity of applied force. In some examples, plurality of capacitance sensors 718 can include a grid (e.g., drive lines and sense lines arranged in rows and columns) of electrodes.

In some examples, capacitance sensors 718 can be located on one side (e.g., top side) of strap 704, and EMG sensors 738 can be located on the other side (e.g., bottom side) of strap 704. Alternatively, capacitance sensors 718 can be interleaved with EMG sensors 738 (not shown).

In some examples, capacitance sensors 718 can be used for hydration (e.g., water and/or sweat) detection for prolonged EMG sensor longevity. When the capacitance sensors 718 detect the hydration, the device can disable or deactivate EMG sensors 738 to prevent from corrosion of the EMG sensors 738 when subject to hydration. The device can optionally inform the user of the hydration conditions and can ask the user to dry the EMG sensors 738. When the capacitance sensors 718 detects a level of hydration less than a predetermined level, the controller or processor can allow activation of EMG sensors 738.

Figure 7B:
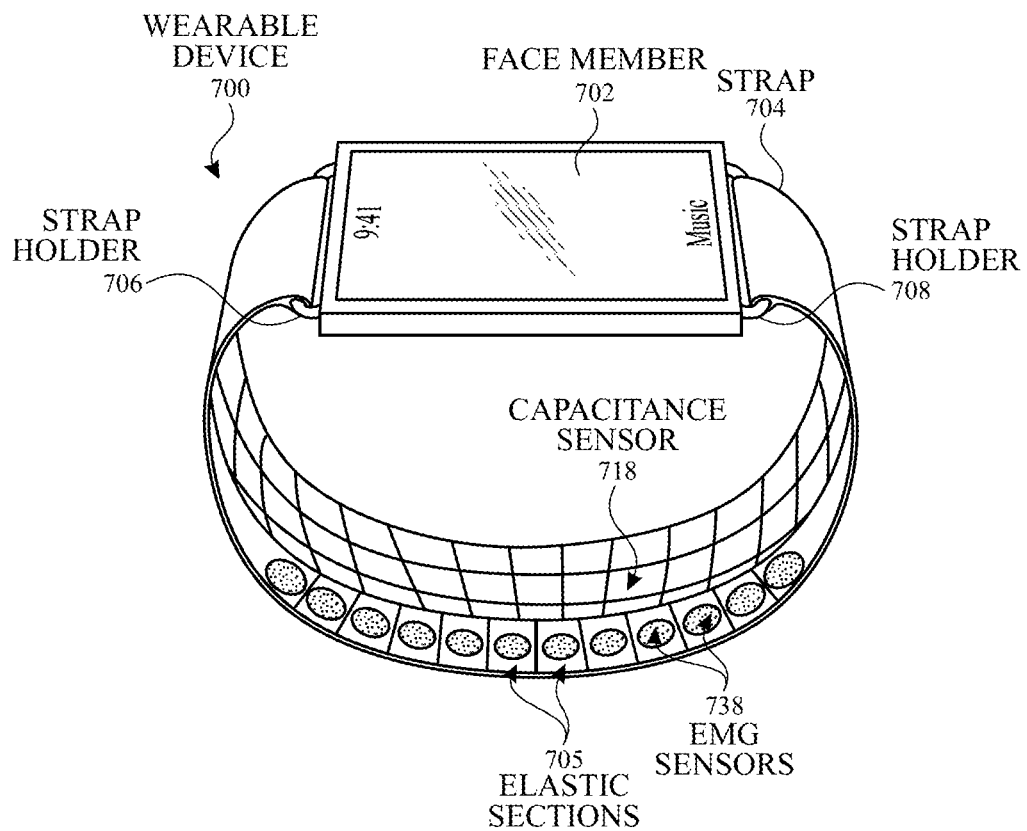
FIG. 7B illustrates a perspective view of an exemplary wearable device having a strap that can include capacitive and sensors and a plurality of elastic sections according to examples of the disclosure.

In some examples, strap 704 can include a plurality of elastic sections, as illustrated in FIG. 7B. Each elastic section 705 can include one or more flex sensors (e.g., flex sensor 350 illustrated in FIG. 3). The flex sensors can be sensors configured to expand when the user's wrist extends, for example. In some example, the flex sensors can be configured to contract when the user's wrist has more tension. The flex sensors can include an elastic material (e.g., elastic strap) or can include at least a partially embedded material. An electrical resistance can be measured across strap 704, the flex sensors, elastic section(s) 705, and/or the partially embedded material. When strap 704 expands, an increase in electrical resistance can be measured; when strap 604 contracts, a decrease in electrical resistance can be measured.

In some examples, one or more of the elastic sections 705 can include one or more EMG sensors 738 disposed on or embedded at least partially within elastic sections 705. In this manner, one elastic section 705 can be coupled to multiple measurement types, such as strain and EMG signals. Moreover, the information from the strain and/or EMG signals can be used in conjunction with information from one or more other sensors (e.g., capacitance sensors 718, optical sensors 362 illustrated in FIG. 3, piezoelectric sensors 452 illustrated in FIG. 4C, accelerometer 342 illustrated in FIG. 3, gyroscopic sensors 346 illustrated in FIG. 3, magnetometer 344 illustrated in FIG. 3, and/or barometric sensor 364 illustrated in FIG. 3) included in the strap and/or watch body to determine one or more user characteristics. For example, wearable device 700 can be capable of generating one or more images of the user's wrist. The images can include information such as amount and/or location of the user's tension (e.g., grip), axial location of the device on the user's wrist, motion and/or rotation of the user's wrist wearable device, vertical location of the user's wrist, and/or muscle activity of the user.

Another exemplary use of the systems and methods disclosed herein can be for weight training. For example, the user can be performing a bicep curl. One or more motion sensors (e.g., accelerometer) can determining the timing of when the user can be performing the bicep curl. The motion sensors can associate the timing with the user's grip of the weights or dumbbells determined by the strain gauges (e.g., piezoelectric sensors). The timing of the bicep curl and user's grip can further be associated with the muscle activity determined by the EMG sensors. The timing of the bicep curl, the user's grip, and the muscle activity can optionally be associated with the user's heart rate determined by, for example, the PPG (e.g., optical sensors) sensors. The device can analyze the user's performance and can provide feedback and/or, for example, calorimetric data related to the user's weight lifting performance. For example, the device can inform the user that the user is over rotating his or her wrist during the exercise and/or is gripping the weights too tightly.

In addition to the one or more sensors disclosed above capable of determining location and performance of the user's wrist, the one or more sensors can give the wearable device capability of automatically self-calibrating the axial location and orientation. For example, instead of prompting the user, each time the wearable device is attached to their wrist, for information regarding which wrist (e.g., left or right) the strap of the wearable device is secured around, the wearable device can determine such information from the one or more sensors disclosed above. For example, a user's left arm (attached to the user's left wrist) can have certain ranges of motion that the user's right arm (attached to the user's right wrist) cannot due to the limited bending angles of each user's elbow joints). The wearable device can utilize information from the EMG sensors, barometric sensors, and/or gyroscopic sensors, to discern between the user's left wrist and right wrist by associating only certain ranges of motion with the user's left wrist and other ranges of motion with the user's right wrist. As another example, the wearable device can automatically detect whether the wearable device body is located on the palm side of the user's wrist using the flex, capacitance, and/or piezoelectric sensors based the location of the user's tendons. In some examples, the device can self-calibrate when the device is first attached to the user's wrist (e.g., detected using the optical and/or capacitance sensors), at certain predetermined intervals (e.g., every 30 minutes), and/or when one or more signal values change (e.g., by more than 10%).

Additionally or alternatively, the wearable device can use one or more sensors for noise reduction and/or cancellation.

For example, adjacent EMG sensors 738 can experience the same amount of electrical activity from the user's muscles. If the signals from the adjacent EMG sensors 738 vary (e.g., a non-zero differential exists), then a processor or controller can utilize the information to subtract, scale, or execute an algorithmic function to reduce or cancel the noise.

Examples of the disclosure can also include systems and methods that can allow a user to control the wireless device and/or host device using movements and/or axial orientation of the wrist. For example, the wearable device can be in communication with a television. The wearable device can recognize one or more gestures and/or sequences that a user can perform as matching one or more predetermined gestures and/or sequences. The wearable device can execute and/or communicate a command associated with the predetermined gesture and/or sequence to commands (e.g., as a substitute for a remote control) to the television.

Examples of the disclosure can also include systems and methods that can be used for authenticating and/or identifying the user based on one or more properties of the user's wrist. Each user can have one or more wrist profiles (e.g., wrist size, tendon locations, wrist shape, etc.). When the user attaches the wearable device to the wrist, a processor or controller can match the wrist profile to a stored wrist profile. The stored wrist profile can be associated with the user and can be used to unlock (i.e., give the user access to full range of functions) the device. In some examples, the stored wrist profiles can be used for restoring calibration settings unique to the user and/or user preferences.

A strap for a wearable device is disclosed. The strap can comprise: an inner side and an outer side; a plurality of strap holders configured to attach to a first edge and a second edge of a wearable device body; and a plurality of capacitance sensors located on the inner side of the strap, the plurality of capacitance sensors configured to sense one or more change in capacitance due to one or more forces of a user's wrist causing one or more changes in capacitance coupling, the plurality of capacitance sensors configured to generate one or more capacitance signals indicative of the one or more changes in capacitance coupling. Additionally or alternatively, in some examples, the strap further comprises: a second plurality of capacitance sensors configured to capacitively couple to the plurality of capacitance sensors and located on the outer side of the strap. Additionally or alternatively, in some examples, the strap further comprises: a plurality of elastic sections, each elastic section including at least one flex sensor, wherein each flex sensor is configured to contract when the user's wrist has more tension and generate one or more signals indicative of the contraction; and a plurality of rigid sections, one or more of the plurality of elastic sections separated by one or more of the plurality of rigid sections. Additionally or alternatively, in some examples, the strap further comprises: a plurality of electromyography sensors configured to measure one or more electrical activities of the user's wrist. Additionally or alternatively, in some examples, the strap further comprises: a plurality of elastic sections, wherein the plurality of electromyography sensors are at least partially embedded in the plurality of elastic sections. Additionally or alternatively, in some examples, the plurality of electromyography sensors is interleaved with the plurality of capacitance sensors. Additionally or alternatively, in some examples, the strap further comprises: one or more piezoelectric sensors configured to measure one or more strains caused by the user's wrist. Additionally or alternatively, in some examples, the strap further comprises: one or more second capacitance sensors configured to capacitively couple to one or more sensors located in a body of a wearable device, wherein the logic is further configured to transmit the one or more capacitance signals to the body of the wearable device using the one or more second capacitance sensors. Additionally or alternatively, in some examples, the plurality of capacitance sensors is arranged as a grid of drive lines and sense lines.

A method of determining a performance of a wrist of a user is disclosed. The method can comprise: determining a tension of the wrist of the user using one or more strain gauges; determining a motion of the wrist using one or more of an accelerometer, gyroscopic sensors, and barometric sensors; and simulating the performance of the wrist using the determined tension and the determined motion. Additionally or alternatively, in some examples, the method further comprises: comparing the simulated performance to a stored one or more ideal performances; and providing the simulation and a performance analysis to the user. Additionally or alternatively, in some examples, the performance is associated with a sports performance and the tension of the wrist includes gripping a sports instrument.

A device is disclosed. The device can comprise: a device body including a top side, an underside, a first edge, and a second edge; a display located on the top side of the device body; a strap comprising: a plurality of strap holders configured to attach to the first and second edges of the device body; an inner side and an outer side; a plurality of strap holders configured to attach to a first edge and a second edge of a wearable device body; a plurality of capacitance sensors located on the inner side of the strap, the plurality of capacitance sensors configured to sense one or more change in capacitance due to one or more forces of a user's wrist causing one or more changes in capacitance coupling, the plurality of capacitance sensors configured to generate one or more capacitance signals indicative of the one or more changes in capacitance coupling; and logic configured to: receive the one or more capacitance signals, and generating one or more capacitance images of the user's wrist from the received on or more capacitance signals, the one or more capacitance images include a two-dimensional representation of location, intensity, or both of the one or more forces. Additionally or alternatively, in some examples, the device is capable of automatic self-calibration, wherein self-calibration includes one or more of determining an axial location and determining an axial orientation of the device body on the wrist of the user.

A method is disclosed. The method can comprise: determining one or more axial orientations of a device body on a wrist of a user, the determination comprising: activating one or more sensors to detect one or more tendons of the user, determining a location of the one or more sensors on the device body or on a strap attached to the device body, and associating the one or more axial orientations to the determination location; and determining one or more axial locations of the device body, the determination comprising: detecting a plurality of motions of the wrist of the user, comparing the detected plurality of motions to one or more stored ranges of motion, and associating the detected plurality of motions to the one or more axial locations. Additionally or alternatively, in some examples, the method further comprises: determining one or more of a shape and a size of the wrist of the user; comparing the determined one or more shape and size of the wrist of the user to one or more stored user profiles; and unlocking the device when the determined one or more shape and size of the wrist of the user match the one or more stored user profiles. Additionally or alternatively, in some examples, the method further comprises: restoring one or more of calibration settings and preferences unique to the user. Additionally or alternatively, in some examples, the determining the one or more axial orientations and the determining the one or more axial locations are automatic. Additionally or alternatively, in some examples, the method further comprises: detecting a coupling of the device body to the user, wherein the determining the one or more axial orientations and the determining the one or more axial locations are performed in response to the detected coupling. Additionally or alternatively, in some examples, the method further comprises: detecting a change in one or more of the one or more axial orientations and one or more axial locations, wherein the determining the one or more axial orientations and the determining the one or more axial locations are performed when an amount of the detected change is greater than a predetermined amount.

Although examples have been fully described with reference to the accompanying drawings, it is to be noted that various changes and modifications will become apparent to those skilled in the art. Such changes and modifications are to be understood as being included within the scope of the various examples as defined by the appended claims.

The invention claimed is:

1. A method of determining a performance of a wrist of a user, the method comprising:
measuring a tension of the wrist of the user using one or more sensors included in a device;
measuring a motion of the wrist using one or more of an accelerometer, a gyroscopic sensor, or a barometric sensor included in the device;
determining the performance of the wrist using the measured tension and the measured motion;
determining a type of the performance;
accessing one or more stored performances corresponding to the type of the performance;
analyzing the performance by comparing the performance to the one or more stored performances; and
providing feedback to the user, the feedback generated from analyzing the performance and configured to show differences between the performance and the one or more stored performances.

2. The method of claim 1, wherein:
the performance is associated with an action performed during a sport; and
the tension corresponds to a grip of a sports instrument.

3. The method of claim 2, wherein:
the sports instrument is a dumbbell; and
the action is lifting the dumbbell.

4. The method of claim 2, wherein:
the one or more sensors include piezoelectric sensors; and
measuring the tension of the wrist comprises:
receiving one or more signals in response to a change in properties of one or more materials included in the piezoelectric sensors; and
determining the tension of the wrist based on the one or more signals.

5. The method of claim 4, further comprising determining a location of the tension by separately receiving and analyzing each of the one or more signals.

6. The method of claim 1, further comprising:
determining a timing of the motion of the wrist; and
associating the timing to the tension, wherein the feedback incorporates the timing.

7. The method of claim 6, further comprising:
determining a muscle activity associated with the motion using one or more electromyography sensors; and
associating the timing and the tension with the muscle activity, wherein the feedback further incorporates the muscle activity.

8. The method of claim 6, further comprising:
determining a heart rate of the user using one or more optical sensors included in the device; and
associating the heart rate with the timing and the tension.

9. The method of claim 1, wherein the feedback includes suggestions on how to improve the performance of the user.

10. The method of claim 1, wherein:
the motion of the wrist comprises a series of movements corresponding to a specific sports motion; and
the specific sports motion includes one or more of swinging a golf club, throwing a football, and lifting a dumbbell.

11. The method of claim 1, where the feedback includes simulating one or more of an acceleration of the wrist and a trajectory of a sports instrument.

12. The method of claim 1, further comprising determining whether the device is located on a left wrist of the user or a right wrist of the user, wherein the determination of whether the device is located on the left wrist or the right wrist comprises:
associating a range of motion with the left wrist and associating another range of motion with the right wrist; and
determining whether the determined motion of the user matches the range of motion of the left wrist or the another range of motion of the right wrist.

13. The method of claim 1, wherein the measurement of the tension of the wrist includes:
measuring a change in electrical resistance; and
determining whether the wrist is expanding or contracting based on the change in electrical resistance.

14. The method of claim 1, wherein:
the one or more sensors include capacitance sensors; and
the measurement of the tension of the wrist includes:
sensing one or more changes in capacitance using the one or more sensors; and
determining whether the wrist is expanding or contracting based on the changes in capacitance.

15. A method comprising:
determining one or more axial orientations of a device body on a wrist of a user by activating one or more sensors to measure a tension of the wrist;
determining one or more axial locations of the device body by activating the one or more sensors to measure a motion of the wrist;
determining a performance of the wrist using the one or more axial orientations and the one or more axial locations;
determining a type of the performance;
accessing a stored performance corresponding to the type of the performance;
comparing the performance to the stored performance; and
providing feedback to the user, the feedback generated by comparing the performance to the stored performance and configured to show differences between the performance and the stored.

16. The method of claim 15, further comprising:
determining one or more of a shape and a size of the wrist of the user;
comparing the determined one or more shape and size of the wrist of the user to one or more stored user profiles; and unlocking the device when the determined one or more shape and size of the wrist of the user match the one or more stored user profiles.

17. The method of claim 16, further comprising restoring one or more of calibration settings and preferences unique to the user.

18. The method of claim 15, wherein the determining the one or more axial orientations and the determining the one or more axial locations are performed automatically.

19. The method of claim 15, further comprising detecting a coupling of the device body to the user, wherein the determining the one or more axial orientations and the determining the one or more axial locations are performed in response to the detected coupling.

20. The method of claim 15, further comprising detecting a change in one or more of the one or more axial orientations and one or more axial locations, wherein the determining the one or more axial orientations and the determining the one or more axial locations are performed when an amount of the detected change is greater than a predetermined amount.

* * * * *

UNITED STATES PATENT AND TRADEMARK OFFICE
CERTIFICATE OF CORRECTION

PATENT NO. : 11,045,117 B2  
APPLICATION NO. : 16/124055  
DATED : June 29, 2021  
INVENTOR(S) : Lor et al.

Page 1 of 1

It is certified that error appears in the above-identified patent and that said Letters Patent is hereby corrected as shown below:

In the Claims

Column 18, Lines 60-61; Claim 15:
"and configured to show differences between the performance and the stored."
Should read as:
--and configured to show differences between the performance and the stored performance.--

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*